US008338641B2

(12) United States Patent
Stöhr et al.

(10) Patent No.: US 8,338,641 B2
(45) Date of Patent: *Dec. 25, 2012

(54) METHOD FOR TREATING ATYPICAL FACIAL PAIN

(75) Inventors: Thomas Stöhr, Monheim (DE); Christine Rauschkolb-Loeffler, Solingen (DE)

(73) Assignee: UCB Pharma GmbH, Monheim (DE)

( * ) Notice: Subject to any disclaimer, the term of this patent is extended or adjusted under 35 U.S.C. 154(b) by 102 days.

This patent is subject to a terminal disclaimer.

(21) Appl. No.: 12/816,753

(22) Filed: Jun. 16, 2010

(65) Prior Publication Data

US 2010/0256241 A1 Oct. 7, 2010

Related U.S. Application Data

(63) Continuation of application No. 11/148,429, filed on Jun. 9, 2005, now Pat. No. 7,820,857.

(60) Provisional application No. 60/578,062, filed on Jun. 9, 2004.

(30) Foreign Application Priority Data

Jun. 9, 2004 (EP) .................................. 04013635

(51) Int. Cl.
C07C 229/00 (2006.01)

(52) U.S. Cl. ................... 562/553; 514/21.91; 514/17.7; 514/18.2; 514/18.3

(58) Field of Classification Search ............... 562/553; 514/21.91, 17.7, 18.2, 18.3
See application file for complete search history.

(56) References Cited

U.S. PATENT DOCUMENTS

| | | | |
|---|---|---|---|
| 5,378,729 A | 1/1995 | Kohn et al. | |
| 5,585,358 A | 12/1996 | Bialer et al. | 514/19 |
| 5,760,038 A | 6/1998 | Murugesan et al. | 514/252 |
| 5,773,475 A | 6/1998 | Kohn | 514/616 |
| 5,885,999 A | 3/1999 | Elliott et al. | 514/258 |
| 6,001,876 A | 12/1999 | Singh | 514/561 |
| 6,037,324 A | 3/2000 | Schwender et al. | 514/18 |
| 6,083,941 A | 7/2000 | Farb | 514/177 |
| 6,083,951 A | 7/2000 | Bradbury | 514/256 |
| 6,114,390 A | 9/2000 | Engel et al. | 514/595 |
| 6,277,825 B1 | 8/2001 | Olivera et al. | 514/13 |
| 6,331,637 B1 | 12/2001 | Chan et al. | 548/241 |
| 6,492,553 B1 | 12/2002 | Hulme et al. | 564/129 |
| 6,727,226 B2 | 4/2004 | Olivera et al. | 514/13 |
| 6,737,408 B1 | 5/2004 | Balasubramanium et al. | 514/18 |
| 6,803,481 B2 | 10/2004 | Selve | 560/157 |
| 6,821,978 B2 | 11/2004 | Chackalamannil et al. | 514/262.1 |
| 6,884,910 B2 | 4/2005 | Harris | 562/553 |
| 7,183,259 B2 | 2/2007 | Scheuerman et al. | 514/18 |
| 7,416,864 B2 | 8/2008 | Stoehr | 435/106 |
| 7,427,601 B2 | 9/2008 | Stoehr | 514/19 |
| 7,687,080 B2 | 3/2010 | Wolicki | 424/725 |
| 7,687,553 B2 | 3/2010 | Beyreuther et al. | 523/115 |
| 7,820,857 B2 | 10/2010 | Stoehr et al. | 562/553 |
| 2002/0052418 A1 | 5/2002 | Shirvan et al. | 514/626 |
| 2004/0204495 A1 | 10/2004 | Shirvan et al. | 514/616 |
| 2004/0220077 A1 | 11/2004 | Selve | 514/1 |
| 2005/0019391 A1 | 1/2005 | Gendrot et al. | 424/464 |
| 2005/0209163 A1 | 9/2005 | Stoehr | 514/19 |
| 2005/0227961 A1 | 10/2005 | Kucharik et al. | 514/211.13 |
| 2006/0100157 A1 | 5/2006 | Rauschkolb-Loffler et al. | 514/18 |
| 2006/0252749 A1 | 11/2006 | Stohr | 514/220 |
| 2007/0042969 A1 | 2/2007 | Rauschkolb-Loffler et al. | 514/19 |
| 2007/0043120 A1 | 2/2007 | Beyreuther et al. | 514/616 |
| 2007/0048372 A1 | 3/2007 | Beyreuther et al. | 424/464 |
| 2007/0054962 A1 | 3/2007 | Selve | 514/575 |
| 2007/0197657 A1 | 8/2007 | Beyreuther et al. | 514/616 |
| 2008/0027137 A1 | 1/2008 | Riedner et al. | 514/561 |
| 2008/0280835 A1 | 11/2008 | Beyreuther et al. | 514/2 |
| 2008/0287545 A1 | 11/2008 | Scheller et al. | 514/616 |
| 2009/0018197 A1 | 1/2009 | Rudd et al. | 514/563 |
| 2009/0018198 A1 | 1/2009 | Stohr | 514/563 |
| 2009/0241205 A1 | 9/2009 | Beyreuther et al. | 800/9 |
| 2010/0029543 A1 | 2/2010 | Beyreuther et al. | 514/2 |
| 2010/0099770 A1 | 4/2010 | Selve | 514/616 |
| 2010/0240576 A1 | 9/2010 | Stoehr | 514/17.7 |
| 2010/0256179 A1 | 10/2010 | Stöhr et al. | 514/327 |
| 2010/0260716 A1 | 10/2010 | Stöhr et al. | 424/85.6 |
| 2010/0273714 A1 | 10/2010 | Stoehr | 514/17.7 |
| 2010/0324144 A1 | 12/2010 | Heers et al. | 514/248 |

FOREIGN PATENT DOCUMENTS

| | | |
|---|---|---|
| EP | 0 555 537 | 8/1993 |
| EP | 0 885 186 | 12/1998 |
| EP | 0 997 147 | 5/2000 |
| EP | 1 077 945 | 2/2001 |
| EP | 1 160 248 | 12/2001 |
| EP | 1 243 263 | 11/2002 |
| EP | 1 486 205 | 12/2004 |
| EP | 1 486 206 | 12/2004 |
| EP | 1 537 862 | 6/2005 |
| EP | 1 541 138 | 6/2005 |
| EP | 1 579 858 | 9/2005 |
| EP | 1 688 137 | 8/2006 |
| WO | WO 96/32100 | 10/1996 |
| WO | WO 99/07413 | 2/1999 |
| WO | WO 99/56761 | 11/1999 |

(Continued)

OTHER PUBLICATIONS

Madland, G., et al. (2001), "Chronic facial pain: a multidisciplinary problem", *J Neurol Neurosurg Psychiatry*, 71:716-719.

Abdulla & Smith (2002) "Changes in Na+ channel currents of rat dorsal root ganglion neurons following axotomy and axotomy-induced autotomy." J. Neurophysiol. 88:2518-2529.

Akiba et al. (2003) "Stable expression and characterization of human PN1 and PN3 sodium channels." Receptors & Channels 9:291-299.

Amir et al. (2006) "The role of sodium channels in chronic inflammatory and neuropathic pain." J. Pain 7(5 Suppl. 3):S1-S29.

Arnér & Meyerson (1988) "Lack of analgesic effect of opioids on neuropathic and idiopathic forms of pain." Pain 33:11-23.

(Continued)

*Primary Examiner* — David Lukton

(74) *Attorney, Agent, or Firm* — Harness, Dickey & Pierce, P.L.C.

(57) ABSTRACT

The present invention is directed to the use of a class of peptide compounds for treating pain in trigeminal neuralgia.

18 Claims, 1 Drawing Sheet

FOREIGN PATENT DOCUMENTS

Figure 1A:
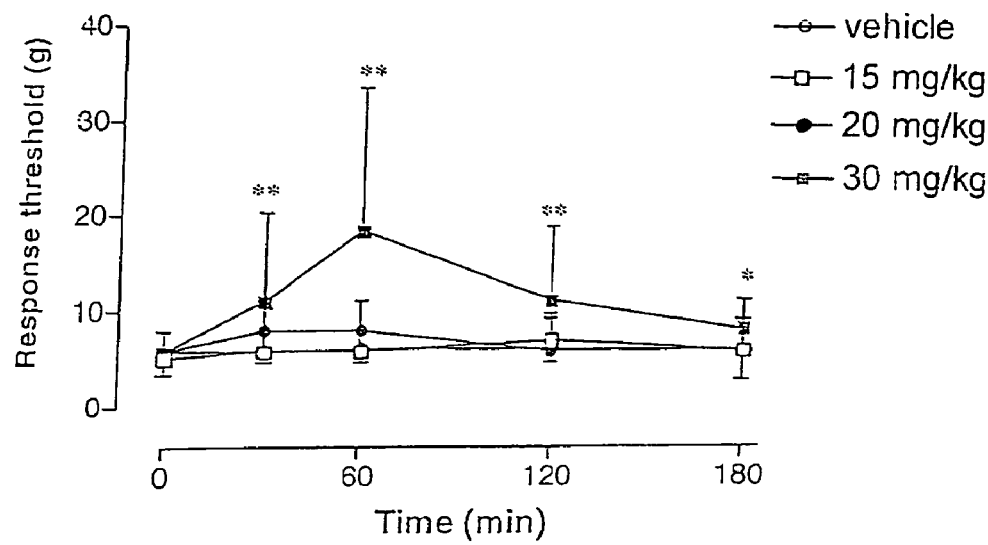

| | | |
|---|---|---|
| WO | WO 00/00463 | 1/2000 |
| WO | WO 00/21509 | 4/2000 |
| WO | WO 00/51586 | 9/2000 |
| WO | WO 01/17976 | 3/2001 |
| WO | WO 01/78762 | 10/2001 |
| WO | WO 02/13766 | 2/2002 |
| WO | WO 02/15922 | 2/2002 |
| WO | WO 02/15937 | 2/2002 |
| WO | WO 02/24698 | 3/2002 |
| WO | WO 02/42256 | 5/2002 |
| WO | WO 02/50051 | 6/2002 |
| WO | WO 02/060863 | 8/2002 |
| WO | WO 02/074297 | 9/2002 |
| WO | WO 02/074784 | 9/2002 |
| WO | WO 02/076979 | 10/2002 |
| WO | WO 03/000642 | 1/2003 |
| WO | WO 03/039520 | 5/2003 |
| WO | WO 03/106482 | 12/2003 |
| WO | WO 2004/043926 | 5/2004 |
| WO | WO 2004/066987 | 8/2004 |
| WO | WO 2004/066990 | 8/2004 |
| WO | WO 2004/100871 | 11/2004 |
| WO | WO 2005/040355 | 5/2005 |
| WO | WO 2005/053667 | 6/2005 |
| WO | WO 2005/092313 | 10/2005 |
| WO | WO 2005/099740 | 10/2005 |
| WO | WO 2005/120539 | 12/2005 |

OTHER PUBLICATIONS

Arroyo (2003) "Safety of SPM 927 in subjects with epilepsy and neuropathic pain" Poster presented at AES Scientific Exhibit, Dec. 5-10, 2003.
Backonja (2002) "Use of anticonvulsants for treatment of neuropathic pain." Neurology 59:S14-S17.
Backonja (2003) "Defining neuropathic pain." Anesth. Analg. 97:785-790.
Béguin et al. (2003) "Functionalized amido ketones: new anticonvulsant agents." Bioorganic & Medicinal Chemistry 11:4275-4285.
Béguin et al. (2004) "N-Substituted amino acid N'-benzylamides: synthesis, anticonvulsant, and metabolic activities." Bioorganic & Medicinal Chemistry 12:3079-3096.
Bennett & Xie (1988) "A peripheral mononeuropathy in rat that produces disorders of pain sensation like those seen in man." Pain 33(1):87-107 (abstract only www.ncbi.nlm.nih.gov/pubmed/2837713).
Bennett et al. (2000) "Alleviation of mechanical and thermal allodynia by $CGRP_{8-37}$ in a rodent model of chronic central pain." Pain 86:163-175.
Benoist et al. (1999) Exp. Brain. Res. 126:383-398.
Beyak et al. (2004) "Two TTX-resistant Na+ currents in mouse colonic dorsal root ganglia neurons and their role in colitis-induced hyperecitability." Am. J. Physiol. Gastrointest. Liver Physiol. 287:G845-G855.
Beyreuther (2004) "Pharmacology of SPM 927 and its relevance to clinical practice for neuropathic pain" Presented at Visiongain Pain Management, 2004.
Beyreuther et al. (2004) "SPM 927 displays potent antinociceptive effects in rat models for inflammatory and neuropathic pain" Poster presented at Neuropathic Pain, May 13-14, 2004.
Beyreuther et al. (2006) "Effects of lacosamide as compared to other analgesics: a responder analysis in the streptozotocin rat model for diabetic neuropathic pain" Poster 618 presented at American Pain Society, 2006 (abstract at www.ampainsoc.org/db2/abstract/view?poster_id=2637#618).
Beyreuther et al. (2006) "Antinociceptive efficacy of lacosamide in a rat model for painful diabetic neuropathy." Eur. J. Pharmacol. 539:64-70.
Beyreuther et al. (2007) "Lacosamide: A review of preclinical properties." CNS Drug Rev. 13(1):21-42.
Beyreuther et al. (2007) Arthritis Res. Therapy 9:R14, arthritis-research.com/content/9/1/R14.
Bialer et al. (2001) "Progress report on new antiepileptic drugs: a summary of the Fifth Eilat Conference (EILAT V)." Epilepsy Res. 43:11-58.
Bialer et al. (2002) "Progress report on new antiepileptic drugs: a summary of the Sixth Eilat Conference (EILAT VI)." Epilepsy Res. 51:31-71.
Biton et al. (2003) "Safety and efficacy of SPM 927 during the initial phase of an extension trial in subjects with partial seizures." Epilepsia 44(Suppl. 9):259, abst. 2.241 (poster attached).
Blackburn-Munro et al. (2002) "A comparison of the anti-nociceptive effects of voltage-activated Na+ channel blockers in the formalin test." Eur. J. Pharmacol. 445:231-238.
Bretschneider et al. (2006) "A multi-center, open-label, follow-on trial to assess the long-term safety and efficacy of lacosamide in subjects with painful distal diabetic neuropathy." www.ampainsoc.org/db2/abstract/view?poster_id=2765#766.
Cawello et al. (2003) "No influence of the new antiepileptic drug SPM 927 on the ECG time intervals QTc and PR." Epilepsia 44(Suppl. 9):95, abst. 1.265 (poster attached).
Cawello et al. (2004) "Food does not affect the pharmacokinetics of SPM 927." Epilepsia 45(Suppl. 7):307, abst. 2.342 (poster attached).
Chevrier et al. (2004) "Differential modulation of $Na_v1.7$ and $Na_v1.8$ peripheral nerve sodium channels by the local anesthetic lidocaine." Br. J. Pharmacol. 142:576-584.
Chipkin (2005) Am. J. Med. 118(5A):4S-13S.
Cummins et al. (2004) "Electrophysiological properties of mutant $Na_v1.7$ sodium channels in a painful inherited neuropathy." J. Neurosci. 24(38):8232-8236.
Decosterd & Woolf (2000) "Spared nerve injury: an animal model of persistent peripheral neuropathic pain." Pain 87:149-158.
Doty et al. (2004) in Bialer et al. "Progress report on new antiepileptic drugs: a summary of the Seventh Eilat Conference (EILAT VII)." Epilepsy Res. 61:1-48, pp. 14-16.
Doty et al. (2004) "Update on the clinical development of SPM 927 (formerly harkoseride)" Presented at EILAT VII, May 2004.
Dowdall et al. (2005) "Comparison of five different rat models of peripheral nerve injury." Pharmacol. Biochem. Behavior 80:93-108.
Dubuisson & Dennis (1977) "The Formalin Test: A quantitative study of the analgesic effects of morphine, meperidine, and brain stem stimulation in rats and cats." Pain 4:161-174.
Duncan & Kohn (2005) "The novel antiepileptic drug lacosamide blocks behavioral and brain metabolic manifestations of seizure activity in the 6 Hz psychomotor seizure model." Epilepsy Res. 67:81-87.
Eller et al. (2005) "Trigeminal neuralgia: definition and classification." Neurosurg. Focus 18(5):E3, 3 pp.
Elliott (1997) "Slow Na+ channel inactivation and bursting discharge in a simple model axon: implications for neuropathic pain." Brain Res. 754:221-226.
Erichsen & Blackburn-Munro (2002) "Pharmacological characterisation of the spared nerve injury model of neuropathic pain." Pain 98:151-161.
Everill et al. (2001) "Sodium currents of large (Aβ-type) adult cutaneous afferent dorsal root ganglion neurons display rapid recovery from inactivation before and after axotomy." Neurosci. 106(1):161-169.
Field et al. (1997) "Gabapentin (neurontin) and S-(+)-3-isobutylgaba represent a novel class of selective antihyperalgesic agents." Br. J. Pharmacol. 121:1513-1522.
Field et al. (2002) "Gabapentin and the $neurokinin_1$ receptor antagonist CI-1021 act synergistically in two rat models of neuropathic pain." J. Pharmacol. Exp. Ther. 303(2):730-735.
Fisher, et al. (2003) "Trigeminal Neuralgia: current treatments and future developments." Expert Opin. Emerging Drugs 8(1):123-143.
Freynhagen et al. (2005) "Efficacy of pregabalin in neuropathic pain evaluated in a 12-week randomised, double-blind, multicentre, placebo-controlled trial of flexible- and fixed-dose regimens." Pain 115:254-263.
Hama et al. (1999) "NMDA-induced spinal hypersensitivity is reduced by naturally derived peptide analog [$ser^1$] histogranin." Pharmacol. Biochem. Behavior 62(1):67-74.
Han et al. (2000) "Characteristics of ectopic discharges in a rat neuropathic pain model." Pain 84:253-261.

Hao et al. (2004) "SPM 927, a new anti-epileptic drug, alleviates neuropathic pain-like behaviors in rats after spinal cord or trigeminal nerve injury" Poster presented at Neuropathic Pain—Changing Paradigms in Diagnosis and Treatment, Madrid, May 2004.

Hidvegi et al. (2006) "Lacosamide in subjects with painful distal diabetic neuropathy: results of a multi-center, open-label, follow-on trial" Poster presented at American Pain Society, May 3-6, 2006.

Hofmann et al. (2003) "Pharmacological sensitivity and gene expression analysis of the tibial nerve injury model of neuropathic pain." Eur. J. Pharmacol. 470:17-25.

Hong et al. (2004) "Early painful diabetic neuropathy is associated with differential changes in tetrodotoxin-sensitive and -resistant sodium channels in dorsal root ganglion neurons in the rat." J. Biol. Chem. 279(28):29341-29350.

Honore et al. (2000) "Murine models of inflammatory, neuropathic and cancer pain each generates a unique set of neurochemical changes in the spinal cord and sensory neurons." Neurosci. 98(3):585-598.

Horstmann et al. (2002) "Basic clinical pharmacological investigations of the new antiepileptic drug SPM 927." Epilepsia 43(Suppl. 7):188, abst. 2.174 (poster attached).

Horstmann et al. (2003) "SPM 927 does not interact with valproic acid and carbamazepine." Epilepsia 44(Suppl. 9):97, Abst. 1.271 (poster attached).

Horstmann et al. (2003) "SPM 927 does not prolong the QTc interval" Poster presented at 6th International Conference on the Mechanisms and Treatment of Neuropathic Pain, San Francisco, Sep. 18-20, 2003.

Hovinga (2003) "SPM-927 (Erlosamide Schwarz Pharma)." IDRUGS: The Investigational Drugs Journal 6(5):479-485.

Hovinga (2002) "Novel anticonvulsant medications in development." Expert Opin. Investig. Drugs 11(10) 1387-1406.

Hunt (2003) "Musculoskeletal fitness: the keystone in overall wellbeing and injury prevention." Clin. Orthopaedics Rel. Res. 409:96-105.

Hurley et al. (2002) "Gabapentin and pregabalin can interact synergistically with naproxen to produce antihyperalgesia." Anesthesiology 97:1263-1273.

Ilyin et al. (2005) "V102862 (Co 102862): a potent, broad-spectrum state-dependent blocker of mammalian voltage-gated sodium channels." Br. J. Pharmacol. 144:801-812.

Jain (2000) "A guide to drug evaluation for chronic pain." Emerging Drugs 5(2):241-257.

Jensen (2000) "Assessment and treatment of neuropathic pain." Eur. J. Neurol. 7(Suppl. 3):3-4, abst. MT-9.

Josepha et al. (2004) "Novel mechanism of enhanced nociception in a model of AIDS therapy-induced painful peripheral neuropathy in the rat." Pain 107:147-158.

Kelso (2005) "Sodium channel blockers in neuropathic pain." Curr. Pharm. Design 11.

Kenney et al. (2006) enney et al. (2006) "A multi-center, randomized, double-blind, placebo-controlled trial assess the efficacy and safety of lacosamide (200, 400, and 600 mg/day) in subjects with painful distal diabetic neuropathy." www.ampainsoc.org/db2/abstract/view?poster_id=2773#774.

Kim & Chung (1992) "An experimental model for peripheral neuropathy produced by segmental spinal nerve ligation in the rat." Pain 50(3):355-363.

Kohn et al. (1991) "Preparation and anticonvulsant activity of a series of functionalized α-heteroatom-substituted amino acids." J. Med. Chem. 34:2444-2452.

Kropeit et al. (2004) "Bioequivalence of short-time infusions compared to oral administration of SPM 927." Epilepsia 45(Suppl. 7): 123, abst. 1.323 (poster attached).

Lai et al. (2003) "The role of voltage-gated sodium channels in neuropathic pain." Curr. Opin. Neurobiol. 13:291-297.

Lai et al. (2004) "Voltage-gated sodium channels and hyperalgesia." Ann. Rev. Pharmacol. Toxicol. 44:371-397.

Lampert et al. (2006) "Upregulation of persistent and ramp sodium current in dorsal horn neurons after spinal cord injury." Exp. Brain Res. 174(4):660-666.

Lawand et al. (1997) "Excitatory amino acid receptor involvement in peripheral nociceptive transmission in rats." Eur. J. Pharmacol. 324:169-177.

Lee et al. (2000) "An animal model of neuropathic pain employing injury to the sciatic nerve branches." NeuroReport 11(4):657-661.

Lee & Jeong (2002) "Effects of different concentrations of formalin on paw edema and pain behaviors in rats." J. Korean Med. Sci. 17:81-85.

Lesser et al. (2004) "Pregabalin relieves symptoms of painful diabetic neuropathy." Neurology 63:2104-2110.

LeTiran et al. (2002) "Design and evaluation of affinity labels of functionalized amino acid anticonvulsants." J. Med. Chem. 45:4762-4773.

Lockwood et al. (2002) "Tinnitus." N. Engl. J. Med. 347(12):904-910.

Lowry & Richardson (1976), *Mechanism and Theory in Organic Chemistry*, Harper & Row, New York, pp. 60-70.

Lu & Westlund (1999) "Gabapentin attenuates nociceptive behaviors in an acute arthritis model in rats." J. Pharmacol. Exp. Ther. 290(1):214-219.

Lynch et al. (2004) "Attenuation of mechanical allodynia by clinically utilized drugs in a rat chemotherapy-induced neuropathic pain model." Pain 110(1-2):56-63.

Macres (2000) "Understanding neuropathic pain" www.spineuniverse.com/displayarticle.php/article1614._html [retrieved on Nov. 30, 2007] pp. 1-8.

Maier et al. (2004) "A pilot randomized, double-blind, placebo-controlled pilot trial to investigate safety and efficacy of SPM 927 in subjects with postherpetic neuralgia" Poster presented at Neuropathic Pain, May 13-14, 2004.

Majumdar et al. (2004) "Induction of pseudo-periodic oscillation in voltage-gated sodium channel properties is dependent on the duration of prolonged depolarization." Eur. J. Neurosci. 20:127-143.

Mar. 1985 Advanced Organic Chemistry: Reactions, Mechanisms, and Structure. New York: Wiley, pp. 16-18.

McCleane et al. (2003) "Does SPM 927 have an analgesic effect in human neuropathic pain? An open label study." Neurosci. Lett. 352:117-120.

McCleane (2003) "Pharmacological management of neuropathic pain." CNS Drugs 17(14):1031-1043.

Moller (2000) "Similarities between severe tinnitus and chronic pain." J. Am. Acad. Audiol. 11(3):115-124.

Morrow et al. (2001) "Antinociceptive properties of the anticonvulsant SPM927 (Harkoseride) in rat." Soc. Neurosci. Conf. Abst. 508.16, 27(1):1332.

Patel et al. (2001) "The effects of $GABA_B$ agonists and gabapentin on mechanical hyperalgesia in models of neuropathic and inflammatory pain in the rat." Pain 90:217-226.

Priestley (2004) "Voltage-gated sodium channels and pain." Curr. Drug Targets—CNS & Neurol. Disorders 3:441-456.

Rauck et al. (2003) "A randomized, double-blind, placebo-controlled trial to investigate the safety and efficacy of SPM 927 in painful diabetic neuropathy" Poster presented at 6th Int. Conf. on Mechanisms and Treatment of Neuropathic Pain, Sep. 2003.

Rauck et al. (2007) "Lacosamide in painful diabetic peripheral neuropathy. A phase 2 double-blind placebo-controlled study." Clin. J. Pain 23(2):150-158.

Rauschkolb et al. (2004) "SPM 927, a novel promising pain treatment" Presented at Visiongain Pain Management, 2004.

Richeimer (2000) "The Richeimer Pain Update" www.helpforpain.com/arch2000dec.htm.

Rodger (1991) "Non-insulin-dependent (type II) diabetes mellitus." Can. Med. Assoc. J. 145:1571-1581.

Rosenfeld et al. (2003) "Long-term safety and efficacy of SPM 927 as adjunctive therapy in subjects with partial seizures: 24-week follow-up." Epilepsia 44(Suppl. 9):262, abst. 2.249 (poster attached).

Rosenstock et al. (2004) "Pregabalin for the treatment of painful diabetic peripheral neuropathy: a double-blind, placebo-controlled trial." Pain 110:628-638.

Schiltmeyer et al. (2004) Epilepsia 45(Suppl. 7):313, abst. 2.361 (poster attached).

Schiltmeyer et al. (2006) "No interaction between lacosamide and metformin" Poster 850 presented at American Pain Society 2006 (abstract at www.ampainsoc.org/db2/abstract/view?poster_id=2847_#850).

Seltzer et al. (2001) "Mapping a gene for neuropathic pain-related behavior following peripheral neurectomy in the mouse." Pain 93:101-106.

Shaibani et al. (2005) "An open-label follow-on trial to assess the long-term safety and efficacy of oral lacosamide in subjects with diabetic neuropathy" Poster presented at World Congress on Pain, Aug. 21-26, 2005.

Silver & Soderlund (2005) "State-dependent block of rat $Na_v$ 1.4 sodium channels expressed in xenopus oocytes by pyrazoline-type insecticides." Neurotoxicol. 26:397-406.

Sindrup & Jensen (1999) "Efficacy of pharmacological treatments of neuropathic pain: an update and effect related to mechanism of drug action." Pain 83:389-400.

Sommerville (2003) "Schwarz Pharma's Neurology Pipeline" www.schwarzpharma.com/_uploads/_assets/1369_4_neurology_KNS_190203.pdf.

Stoehr & Beyreuther (2005) "The effect of lacosamide in comparison to other analgesics in rat models for neuropathic pain" Poster presented at 8th Int. Conf. on Mechanisms and Treatment of Neuropathic Pain, San Francisco, Nov. 3-5, 2005.

Tahimic et al. (2006) Biochem. Biophys. Res. Comm. 340:1244-1250.

Teng & Abbott (1998) "The formalin test: a dose-response analysis at three developmental stages." Pain 76:337-347.

Tjølsen & Hole (1997) in Dickinson & Besson, ed., "The Pharmacology of Pain", chap. 1, pp. 1-20; Berlin: Springer-Verlag.

Vos et al. (1994), "Behavioral evidence of trigeminal neuropathic pain following chronic constriction injury to the rat's infraorbital nerve", J. Neurosci., 14:2708-2323.

Wood et al. (2002) in "Sodium Channels and Neuronal Hyperexcitability", pp. 159-172; Chichester: Wiley.

Wood et al. (2004) "Voltage-gated sodium channels and pain pathways." J. Neurobiol. 61:55-71.

Wymer et al. (2005) "A multi-center, randomized double-blind, placebo-controlled trial to assess the efficacy and safety of lacosamide in subjects with painful distal diabetic neuropathy." 8th Int. Conf. on Mechanisms and Treatment of Neuropathic Pain, San Francisco, Nov. 3-5, 2005.

Xu et al. (1992) "Chronic pain-related syndrome in rats after ischemic spinal cord lesion: a possible animal model for pain in patients with spinal cord injury." Pain 48(2):279-290 (abstract only).

Yezierski et al. (1998) "Excitotoxic spinal cord injury: behavioral and morphological characteristics of a central pain model." Pain 75:141-155.

Ziegler et al. (2005) "Efficacy and safety of lacosamide in the treatment of neuropathic pain attributed to distal diabetic neuropathy." 8th Int. Conf. on Mechanisms and Treatment of Neuropathic Pain, San Francisco, Nov. 3-5, 2005.

Office Action, dated Oct. 2, 2006 issued in U.S. Appl. No. 11/148,429.

Office Action, dated Dec. 7, 2007 issued in U.S. Appl. No. 11/148,429.

Office Action, dated Jul. 28, 2008 issued in U.S. Appl. No. 11/148,429.

Office Action, dated Dec. 17, 2009 issued in U.S. Appl. No. 11/148,429.

Office Action, dated Mar. 31, 2009 issued in U.S. Appl. No. 11/342,140.

Office Action, dated Oct. 21, 2009 issued in U.S. Appl. No. 11/342,140.

Office Action, dated Apr. 17, 2009 issued in U.S. Appl. No. 11/507,110.

Office Action, dated Feb. 3, 2010 issued in U.S. Appl. No. 11/507,110.

Office Action, dated Jul. 10, 2008 issued in U.S. Appl. No. 11/507,110.

Office Action, dated Sep. 11, 2007 issued in U.S. Appl. No. 11/507,110.

Office Action, dated Aug. 19, 2010 issued in U.S. Appl. No. 11/507,110.

Office Action, dated Apr. 29, 2009 issued in U.S. Appl. No. 11/506,578.

Office Action, dated Dec. 27, 2007 issued in U.S. Appl. No. 11/506,578.

Office Action, dated Oct. 6, 2008 issued in U.S. Appl. No. 11/506,578.

Office Action, dated Aug. 19, 2009 issued in U.S. Appl. No. 11/000,951.

Office Action, dated Dec. 11, 2007 issued in U.S. Appl. No. 11/000,951.

Office Action, dated Jan. 22, 2009 issued in U.S. Appl. No. 11/000,951.

Office Action, dated Oct. 20, 2006 issued in U.S. Appl. No. 11/000,951.

Office Action, dated Aug. 8, 2007 issued in U.S. Appl. No. 10/466,295.

Office Action, dated Feb. 19, 2009 issued in U.S. Appl. No. 10/466,295.

Office Action, dated Jul. 22, 2009 issued in U.S. Appl. No. 10/466,295.

Office Action, dated Jun. 4, 2008 issued in U.S. Appl. No. 10/466,295.

Office Action, dated Mar. 17, 2010 issued in U.S. Appl. No. 10/466,295.

Office Action, dated Sep. 27, 2006 issued in U.S. Appl. No. 10/466,295.

Office Action, dated Feb. 5, 2007 issued in U.S. Appl. No. 11/149,181.

Office Action, dated Sep. 11, 2006 issued in U.S. Appl. No. 11/149,181.

Office Action, dated Mar. 5, 2007 issued in U.S. Appl. No. 11/129,376.

Office Action, dated Oct. 16, 2007 issued in U.S. Appl. No. 11/129,376.

Office Action, dated Dec. 27, 2007 issued in U.S. Appl. No. 11/506,523.

Office Action, dated Mar. 2, 2010 issued in U.S. Appl. No. 10/599,976.

Office Action, dated Oct. 1, 2010 issued in U.S. Appl. No. 10/599,976.

Office Action, dated Feb. 1, 2011 issued in U.S. Appl. No. 12/643,665.

METHOD FOR TREATING ATYPICAL FACIAL PAIN

This application is a continuation of application Ser. No. 11/148,429, filed on Jun. 9, 2005 now U.S. Pat. No. 7,820,857, which claims the benefit of U.S. provisional application Ser. No. 60/578,062 filed on Jun. 9, 2004 and European patent application No. 04013635.0 filed on Jun. 9, 2004. Each of the above referenced applications is incorporated herein by reference in its entirety.

The present invention is directed to the use of a class of peptide compounds for treating pain in trigeminal neuralgia.

Certain peptides are known to exhibit central nervous system (CNS) activity and are useful in the treatment of epilepsy and other CNS disorders. These peptides which are described in the U.S. Pat. No. 5,378,729 have the Formula (Ia):

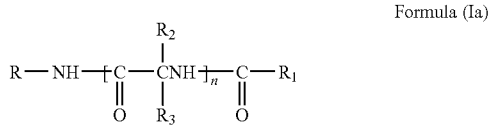

Formula (Ia)

wherein
R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;
$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and
$R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z—Y wherein $R_2$ and $R_3$ may be unsubstituted or substituted with at least one electron withdrawing group or electron donating group;
Z is O, S, S(O)$_a$, NR$_4$, PR$_4$ or a chemical bond;
Y is hydrogen, lower alkyl, aryl, aryl lower alkyl, lower alkenyl, lower alkynyl, halo, heterocyclic, heterocyclic lower alkyl, and Y may be unsubstituted or substituted with an electron donating group or an electron withdrawing group, provided that when Y is halo, Z is a chemical bond, or
ZY taken together is NR$_4$NR$_5$R$_7$, NR$_4$OR$_8$, ONR$_4$R$_7$, OPR$_4$R$_5$, PR$_4$OR$_5$, SNR$_4$R$_7$, NR$_4$SR$_7$, SPR$_4$R$_5$ or PR$_4$SR$_7$, NR$_4$PR$_5$R$_6$ or PR$_4$NR$_5$R$_7$,

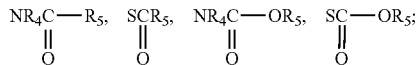

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group; and
$R_7$ is $R_6$ or COOR$_8$ or COR$_8$;
$R_8$ is hydrogen or lower alkyl, or aryl lower alkyl, and the aryl or alkyl group may be unsubstituted or substituted with an electron withdrawing group or an electron donating group; and
n is 1-4; and
a is 1-3.

U.S. Pat. No. 5,773,475 also discloses additional compounds useful for treating CNS disorders. These compounds are N-benzyl-2-amino-3-methoxy-propionamide having the Formula (IIa):

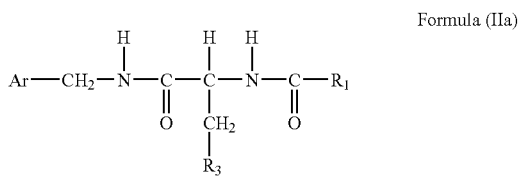

Formula (IIa)

wherein
Ar is aryl which is unsubstituted or substituted with halo; $R_3$ is lower alkoxy; and $R_1$ is methyl.

U.S. Pat. No. 5,378,729 and U.S. Pat. No. 5,773,475 are hereby incorporated by reference. However, neither of these patents describes the use of these compounds as specific analgesics for the treatment of pain in trigeminal neuralgia.

WO 02/074297 relates to the use of a compound according to Formula (IIa) wherein Ar is phenyl which may be substituted by at least one halo, $R_3$ is lower alkoxy containing 1-3 carbon atoms and $R_1$ is methyl for the preparation of pharmaceutical compositions useful for the treatment of allodynia related to peripheral neuropathic pain.

WO 02/074784 relates to the use of a compound having Formula (Ia) or/and Formula (IIa) showing antinociceptive properties for treating different types and symptoms of acute and chronic pain, especially non neuropathic inflammatory pain, e.g. rheumatoid arthritic pain or/and secondary inflammatory osteo-arthritic pain.

Pain is a subjective experience and the perception of pain is performed in particular parts of the Central Nervous System (CNS). Usually noxious (peripheral) stimuli are transmitted to the Central Nervous System (CNS) beforehand, but pain is not always associated with nociception. A broad variety of different types of clinical pain exists, that are derived from different underlying pathophysiological mechanisms and that will need different treatment approaches.

The perception of pain may be characterized by three major types of clinical pain:
acute pain
chronic pain
neuropathic pain Acute clinical pain may result from inflammation or soft tissue injury, for instance. This type of pain is adaptive and has the biologically relevant function of warning and enabling healing and repair of an already damaged body part to occur undisturbed. A protective function is achieved by making the injured/inflamed area and surrounding tissue hypersensitive to all stimuli so that contact with any external stimulus is avoided. The neuronal mechanisms underlying this type of clinical pain are fairly well understood and pharmacological control of acute clinical pain is available and effective by means of e.g. Non-Steroidal Anti-Inflammatory Drugs (NSAIDs) up to opioids depending on type and extension of the sensation.

Chronic clinical pain appears as sustained sensory abnormalities resulting from an ongoing peripheral pathology such as cancer or chronic inflammation (e.g. arthritis) or it can be independent of the initiating triggers. The latter being maladaptive, offering no survival advantage and very often no effective treatment is available.

There are several causes of human neuropathy with considerable variability in symptoms and neurological deficits. Painful neuropathies are defined as neurological disorders characterised by persistence of pain and hypersensitivity in a body region, of which the sensory innervation has been damaged, but damage to sensory nerves does not always produce neuropathic pain, usually loss of sensation rather than hypersensitivity or pain are observed.

Neuropathic pain can be classified as peripheral and central neuropathic pain. Peripheral neuropathic pain is caused by injury or infection of peripheral sensory nerves, whereas central neuropathic pain is caused by damage to the CNS or/and the spinal cord. Both peripheral and central neuropathic pain can occur without obvious initial nerve damage.

Common analgesics like opioids and non-steroidal anti-inflammatory drugs (NSAIDs) improve only insufficiently chronic abnormal pain syndromes as peripheral and central neuropathic pain due to insufficient efficacy or limiting side effects. In the search for alternative treatment regimes to produce satisfactory and sustained pain relief, corticosteroids, conduction blockade, glycerol, antidepressants, local anesthetics, gangliosides and electrostimulation have been tried, but mainly anti-convulsants have been found useful against various types of peripheral neuropathic pain conditions. A subset of patients with neuropathic pain responds to opioids. Carbamazepine is effective in reducing pain in patients with trigeminal neuralgia.

If general overactivity and unleaded low threshold activation of sensory neurons is considered as one of the main syndromes of neuropathy and neuropathic pain sensation with a marked mechanoallodynia as the most disabling clinical symptom, selective inhibition of this pathophysiological event instead of general inhibition of high threshold noxious stimuli (by e.g. local anesthetics) of the normal sensory nociception provides clear advantages.

The mechanisms of trigeminal neuralgia are poorly understood. Current treatments use a variety of pharmacological, surgical, physical and psychological approaches. However, the evidence for many of the treatments is still limited. Mononeuropathies in general can be caused by any trauma or lesion or may even exist without a known cause, as is very often the case with atypical facial pain.

The use of compounds of Formula (Ib) or/and Formula (IIb) for treatment of pain in trigeminal neuralgia has not been reported. Thus, the present invention concerns the use of said compounds of Formulae (Ib) or/and (IIb) for the preparation of a pharmaceutical composition for the prevention, alleviation or/and treatment of trigeminal neuropathic pain and other forms of mononeuropathies or atypical facial pain.

Surprisingly, application of compounds (Ib) or/and (IIb), particularly (R)-2-acetamide-N-benzyl-3-methoxypropionamide (SPM 927) exhibited a significant efficacy in reducing mechanical hypersensitivity in rats with infraorbital nerve injury. Thus, the compounds are useful as analgesic or/and anti-allodynic compounds for treating trigeminal neuropathic pain. Treatment with SPM 927 particularly leads to a significant increase in the response threshold indicating analgesic or/and anti-allodynic activity in trigeminal neuralgia.

A compound according to the invention has the general Formula (Ib)

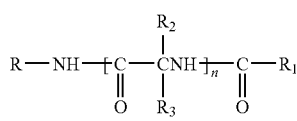

Formula (Ib)

wherein
R is hydrogen, lower alkyl, lower alkenyl, lower alkynyl, aryl, aryl lower alkyl, heterocyclic, heterocyclic lower alkyl, lower alkyl heterocyclic, lower cycloalkyl or lower cycloalkyl lower alkyl, and R is unsubstituted or is substituted with at least one electron withdrawing group, and/or at least one electron donating group;

$R_1$ is hydrogen or lower alkyl, lower alkenyl, lower alkynyl, aryl lower alkyl, aryl, heterocyclic lower alkyl, lower alkyl heterocyclic, heterocyclic, lower cycloalkyl, lower cycloalkyl lower alkyl, each unsubstituted or substituted with at least one electron donating group and/or at least one electron withdrawing group;
and
$R_2$ and $R_3$ are independently hydrogen, lower alkyl, lower alkenyl, lower alkynyl, aryl lower alkyl, aryl, halo, heterocyclic, heterocyclic lower alkyl, lower alkyl heterocyclic, lower cycloalkyl, lower cycloalkyl lower alkyl, or Z—Y wherein $R_2$ and $R_3$ may be unsubstituted or substituted with at least one electron withdrawing group and/or at least one electron donating group;

Z is O, S, S(O)$_a$, NR$_4$, NR'$_6$, PR$_4$ or a chemical bond;
Y is hydrogen, lower alkyl, aryl, aryl lower alkyl, lower alkenyl, lower alkynyl, halo, heterocyclic, heterocyclic lower alkyl, lower alkyl heterocyclic and Y may be unsubstituted or substituted with at least one electron donating group and/or at least one electron withdrawing group, provided that when Y is halo, Z is a chemical bond, or ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$, PR$_4$SR$_7$, NR$_4$PR$_5$R$_6$, PR$_4$NR$_5$R$_7$ or N$^+$R$_5$R$_6$R$_7$,

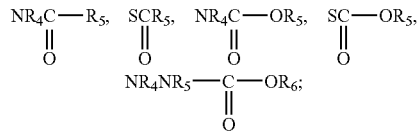

R'$_6$ is hydrogen, lower alkyl, lower alkenyl, or lower alkenyl which may be unsubstituted or substituted with at least one electron withdrawing group or/and at least one electron donating group;

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may independently be unsubstituted or substituted with at least one electron withdrawing group or/and at least one electron donating group;

$R_7$ is $R_5$ or COOR$_8$ or COR$_8$, which $R_7$ may be unsubstituted or substituted with at least one electron withdrawing group or/and at least one electron donating group;

$R_8$ is hydrogen or lower alkyl, or aryl lower alkyl, and the aryl or alkyl group may be unsubstituted or substituted with at least one electron withdrawing group or/and at least one electron donating group; and
n is 1-4; and
a is 1-3.

Preferably the compound according has the general Formula (IIb)

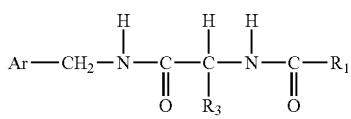

Formula (IIb)

wherein
Ar is aryl, especially phenyl, which is unsubstituted or substituted with at least one halo; $R_3$ is —$CH_2$-Q, wherein Q is lower alkoxy; and $R_1$ is lower alkyl, especially methyl.

The present invention is also directed to a pharmaceutical composition comprising a compound according to Formula (Ib) or/and Formula (IIb) useful for the prevention, alleviation or/and treatment of trigeminal neuropathic pain.

The "lower alkyl" groups when used alone or in combination with other groups, are lower alkyl containing from 1 to 6 carbon atoms, especially 1 to 3 carbon atoms, and may be straight chain or branched. These groups include methyl, ethyl, propyl, isopropyl, butyl, isobutyl, tertiary butyl, amyl, hexyl, and the like.

The "lower alkoxy" groups are lower alkoxy containing from 1 to 6 carbon atoms, especially 1 to 3 carbon atoms, and may be straight chain or branched. These groups include methoxy, ethoxy, propoxy, butoxy, isobutoxy, tert-butoxy, pentoxy, hexoxy and the like.

The "aryl lower alkyl" groups include, for example, benzyl, phenylethyl, phenylpropyl, phenylisopropyl, phenylbutyl, diphenylmethyl, 1,1-diphenylethyl, 1,2-diphenylethyl, and the like.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. A polynuclear aromatic compound as used herein, is meant to encompass bicyclic and tricyclic fused aromatic ring systems containing from 10-18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocenyl. Aryl groups may be unsubstituted or mono or polysubstituted with electron withdrawing or/and electron donating groups as described below.

"Lower alkenyl" is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like.

The term "lower alkynyl" is an alkynyl group containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "lower cycloalkyl" when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Cycloalkyl groups may be unsubstituted or mono or polysubstituted with electron withdrawing or/and electron donating groups as described below. Furthermore, the substituents may either be in endo or exo positions in the bridged bicyclic systems.

The term "electron-withdrawing and electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16-18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, haloalkyl such as trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl) amino, aryloxy such as phenoxy, mercapto, lower alkylthio, lower alkylmercapto, disulfide (lower alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The term "halo" includes fluoro, chloro, bromo, iodo and the like.

The term "acyl" includes lower alkanoyl containing from 1 to 6 carbon atoms and may be straight chains or branched. These groups include, for example, formyl, acetyl, propionyl, butyryl, isobutyryl, tertiary butyryl, pentanoyl and hexanoyl.

As employed herein, a heterocyclic group contains at least one sulfur, nitrogen or oxygen ring atom, but also may include several of said atoms in the ring. The heterocyclic groups contemplated by the present invention include heteroaromatics and saturated and partially saturated heterocyclic compounds. These heterocyclics may be monocyclic, bicyclic, tricyclic or polycyclic and are fused rings. They may preferably contain up to 18 ring atoms and up to a total of 17 ring carbon atoms and a total of up to 25 carbon atoms. The heterocyclics are also intended to include the so-called benzoheterocyclics. Representative heterocyclics include furyl, thienyl, pyrazolyl, pyrrolyl, methylpyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the N-oxides of pyridyl, pyrazinyl, and pyrimidinyl and the like. Heterocyclic groups may be unsubstituted or mono or polysubstituted with electron withdrawing or/and electron donating groups.

The preferred heterocyclics are thienyl, furyl, pyrrolyl, benzofuryl, benzothienyl, indolyl, methylpyrrolyl, morpholinyl, pyridiyl, pyrazinyl, imidazolyl, pyrimidinyl, or pyridazinyl. The preferred heterocyclic is a 5 or 6-membered heterocyclic compound. The especially preferred heterocyclic is furyl, pyridyl, pyrazinyl, imidazolyl, pyrimidinyl, or pyridazinyl. The most preferred heterocyclics are furyl and pyridyl.

The preferred compounds are those wherein n is 1, but di (n=2), tri (n=3) and tetrapeptides (n=4) are also contemplated to be within the scope of the invention.

The preferred values of R is aryl lower alkyl, especially benzyl, especially those wherein the phenyl ring thereof is unsubstituted or substituted with electron donating groups or/and electron withdrawing groups, such as halo (e.g., F).

The preferred $R_1$ is H or lower alkyl. The most preferred $R_1$ group is methyl.

The preferred electron donating substituents or/and electron withdrawing substituents are halo, nitro, alkanoyl, formyl, arylalkanoyl, aryloyl, carboxyl, carbalkoxy, carboxamido, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl) amino, amino lower alkyl, mercapto, mercaptoalkyl, alkylthio, and alkyldithio. The term "sulfide" encompasses mercapto, mercapto alkyl and alkylthio, while the term disulfide encompasses alkyldithio. Especially preferred electron donating or/and electron withdrawing groups are halo or lower alkoxy, most preferred are fluoro or methoxy. These preferred substituents may be present on any one of the groups in Formula (Ib) or/and (IIb), e.g. R, $R_1$, $R_2$, $R_3$, $R_4$, $R_5$, $R_6$, $R'_6$, $R_7$, $R_8$ and/or $R_{50}$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein $R_{18}$ is lower alkyl], N-lower alkylhydroxyl amino [(NR$_{18}$)OH wherein $R_{18}$ is lower alkyl], N-lower alkyl-O-lower alkylhydroxyamino, i.e., [N(R$_{18}$)OR$_{19}$ wherein $R_{18}$ and $R_{19}$ are independently lower alkyl], and o-hydroxylamino (—O—NH$_2$); alkylamido such as acetamido; trifluoroacetamido; lower alkoxyamino, (e.g., NH(OCH$_3$)); and heterocyclicamino, such as pyrazoylamino.

The preferred heterocyclic groups representative of $R_2$ and $R_3$ are monocyclic 5- or 6-membered heterocyclic moieties of the formula:

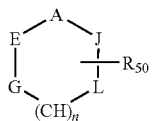

or those corresponding partially or fully saturated form thereof wherein n is 0 or 1; and
$R_{50}$ is H or an electron withdrawing group or electron donating group;
A, E, L, J and G are independently CH, or a heteroatom selected from the group consisting of N, O, S;
but when n is 0, G is CH, or a heteroatom selected from the group consisting of NH, O and S with the proviso that at most two of A, E, L, J and G are heteroatoms.

When n is 0, the above heteroaromatic moiety is a five membered ring, while if n is 1, the heterocyclic moiety is a six membered monocyclic heterocyclic moiety. The preferred heterocyclic moieties are those aforementioned heterocyclics which are monocyclic.

If the ring depicted hereinabove contains a nitrogen ring atom, then the N-oxide forms are also contemplated to be within the scope of the invention.

When $R_2$ or $R_3$ is a heterocyclic of the above formula, it may be bonded to the main chain by a ring carbon atom. When n is 0, $R_2$ or $R_3$ may additionally be bonded to the main chain by a nitrogen ring atom.

Other preferred moieties of $R_2$ and $R_3$ are hydrogen, aryl, e.g., phenyl, aryl alkyl, e.g., benzyl and alkyl.

It is to be understood that the preferred groups of $R_2$ and $R_3$ may be unsubstituted or mono or poly substituted with electron donating or/and electron withdrawing groups. It is preferred that $R_2$ and $R_3$ are independently hydrogen, lower alkyl, which is either unsubstituted or substituted with electron withdrawing groups or/and electron donating groups, such as lower alkoxy (e.g., methoxy, ethoxy, and the like), N-hydroxylamino, N-lower alkylhydroxyamino, N-loweralkyl-O-loweralkyl and alkylhydroxyamino.

It is preferred that one of $R_2$ and $R_3$ is hydrogen.
It is preferred that n is one.
It is more preferred that n=1 and one of $R_2$ and $R_3$ is hydrogen. It is especially preferred that in this embodiment, $R_2$ is hydrogen and $R_3$ is lower alkyl or ZY;
Z is O, NR$_4$ or PR$_4$; Y is hydrogen or lower alkyl; ZY is NR$_4$NR$_5$R$_7$, NR$_4$OR$_5$, ONR$_4$R$_7$,

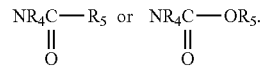

In another especially preferred embodiment, n=1, $R_2$ is hydrogen and $R_3$ is lower alkyl which may be substituted or unsubstituted with an electron donating or electron withdrawing group, NR$_4$OR$_5$, or ONR$_4$R$_7$.

In yet another especially preferred embodiment, n=1, $R_2$ is hydrogen and $R_3$ is lower alkyl which is unsubstituted or substituted with hydroxy or loweralkoxy, NR$_4$OR$_5$ or ONR$_4$R$_7$, wherein $R_4$, $R_5$ and $R_7$ are independently hydrogen or lower alkyl, R is aryl lower alkyl, which aryl group may be unsubstituted or substituted with an electron withdrawing group and $R_1$ is lower alkyl. In this embodiment it is most preferred that aryl is phenyl, which is unsubstituted or substituted with halo.

It is preferred that $R_2$ is hydrogen and $R_3$ is hydrogen, an alkyl group which is unsubstituted or substituted by at least an electron donating or electron withdrawing group or ZY. In this preferred embodiment, it is more preferred that $R_3$ is hydrogen, an alkyl group such as methyl, which is unsubstituted or substituted by an electron donating group, or NR$_4$OR$_5$ or ONR$_4$R$_7$, wherein $R_4$, $R_5$ and $R_7$ are independently hydrogen or lower alkyl. It is preferred that the electron donating group is lower alkoxy, and especially methoxy or ethoxy.

It is preferred that $R_2$ and $R_3$ are independently hydrogen, lower alkyl, or ZY;
Z is O, NR$_4$ or PR$_4$;
Y is hydrogen or lower alkyl or
ZY is NR$_4$R$_5$R$_7$, NR$_4$OR$_5$, ONR$_4$R$_7$,

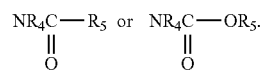

It is also preferred that R is aryl lower alkyl. The most preferred aryl for R is phenyl. The most preferred R group is benzyl. In a preferred embodiment, the aryl group may be unsubstituted or substituted with an electron donating or electron withdrawing group. If the aryl ring in R is substituted, it is most preferred that it is substituted with an electron withdrawing group, especially on the aryl ring. The most preferred electron withdrawing group for R is halo, especially fluoro.

The preferred $R_1$ is lower alkyl, especially methyl.
It is more preferred that R is aryl lower alkyl and $R_1$ is lower alkyl.

Further preferred compounds are compounds of Formula (Ib) wherein n is 1; $R_2$ is hydrogen; $R_3$ is hydrogen, a lower alkyl group, especially methyl which is substituted by an electron donating or electron withdrawing group or ZY; R is aryl, aryl lower alkyl, such as benzyl, wherein the aryl group is unsubstituted or substituted with an electron donating or electron withdrawing group and $R_1$ is lower alkyl. In this embodiment, it is more preferred that $R_3$ is hydrogen, a lower alkyl group, especially methyl, which may be substituted by electron donating group, such as lower alkoxy, (e.g., methoxy, ethoxy and the like), $NR_4OR_5$ or $ONR_4R_7$ wherein these groups are defined hereinabove.

The most preferred compounds utilized are those of the Formula (IIb):

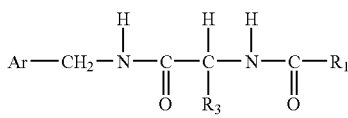

Formula (IIb)

wherein
Ar is aryl, especially phenyl, which is unsubstituted or substituted with at least one electron donating group or electron withdrawing group, especially halo,
$R_1$ is lower alkyl, especially containing 1-3 carbon atoms; and $R_3$ is as defined herein, but especially hydrogen, loweralkyl, which is unsubstituted or substituted by at least an electron donating group or electron withdrawing group or ZY. It is even more preferred that $R_3$ is, in this embodiment, hydrogen, an alkyl group which is unsubstituted or substituted by an electron donating group, $NR_4OR_5$ or $ONR_4R_7$. It is most preferred that $R_3$ is $CH_2$-Q, wherein Q is lower alkoxy, especially containing 1-3 carbon atoms; $NR_4OR_5$ or $ONR_4R_7$ wherein $R_4$ is hydrogen or alkyl containing 1-3 carbon atoms, $R_5$ is hydrogen or alkyl containing 1-3 carbon atoms, and $R_7$ is hydrogen or alkyl containing 1-3 carbon atoms.

The most preferred $R_1$ is $CH_3$. The most preferred $R_3$ is $CH_2$-Q, wherein Q is methoxy.

The most preferred aryl is phenyl. The most preferred halo is fluoro.

The most preferred compounds include:
(R)-2-acetamido-N-benzyl-3-methoxy-propionamide;
O-methyl-N-acetyl-D-serine-m-fluorobenzyl-amide;
O-methyl-N-acetyl-D-serine-p-fluorobenzyl-amide;
N-acetyl-D-phenylglycine benzylamide;
O-1,2-(N,O-dimethylhydroxylamino)-2-acetamide acetic acid benzylamide;
D-1,2-(O-methylhydroxylamino)-2-acetamido acetic acid benzylamide.

It is to be understood that the various combinations and permutations of the Markush groups of $R_1$, $R_2$, $R_3$, R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

The compounds utilized in the present invention may contain one or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atom to which the groups $R_2$ and $R_3$ are attached. When n is 1, the compounds of the present invention is of the formula

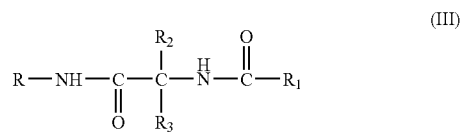

(III)

wherein R, $R_1$, $R_2$, $R_3$, $R_4$, $R_5$, $R_6$, $R'_6$, $R_7$, $R_8$, $R_{50}$ Z and Y are as defined previously.

As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ are attached). These stereoisomers may be found in mixtures of the L and D stereoisomer, e.g., racemic mixtures. The D stereoisomer is preferred.

More preferred is a compound of Formula (III) in the R configuration, preferably substantially enantiopure, wherein the substituent R is benzyl which is unsubstituted or substituted with at least one halo group, wherein $R_3$ is $CH_2$-Q, wherein Q is lower alkoxy containing 1-3 carbon atoms and wherein $R_1$ is methyl. Preferably R is unsubstituted benzyl or benzyl substituted with at least one halo group which is a fluoro group.

Depending upon the substituents, the present compounds may form addition salts as well. All of these forms are contemplated to be within the scope of this invention including mixtures of the stereoisomeric forms.

The manufacture of the utilized compounds is described in U.S. Pat. Nos. 5,378,729 and 5,773.475, the contents of both of which are incorporated by reference.

The compounds utilized in the present invention are useful as such as depicted in the Formulae (Ib) or/and (IIb) or can be employed in the form of salts in view of its basic nature by the presence of the free amino group. Thus, the compounds of Formulae (Ib) or/and (IIb) form salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

The present invention is further directed to a method for the prevention, alleviation or/and treatment of a disease or condition as described above in a mammal, including a human being, comprising administering at least one compound of Formulae (Ib) or/and (IIb).

It is preferred that the compound utilized in the present invention is used in therapeutically effective amounts.

The physician will determine the dosage of the present therapeutic agents which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

In a preferred embodiment, the compounds of the present invention are administered in amounts ranging from about 1 mg to about 100 mg per kilogram of body weight per day, more preferably in amounts ranging from about 1 mg to about 10 mg per kilogram of body weight per day. This dosage regimen may be adjusted by the physician to provide the optimum therapeutic response. Patients in need thereof may be treated with doses of the compound of the present invention of at least 50 mg/day, preferably of at least 200 mg/day, more preferably of at least 300 mg/day and most preferably of at least 400 mg/day. For example, a patient in need thereof may be treated with doses at a maximum of 6 g/day, more preferably a maximum of 1 g/day and most preferably a maximum of 600 mg/day. In some cases, however, lower or higher doses may be needed.

In another preferred embodiment, the daily doses are increased until a predetermined daily dose is reached which is maintained during the further treatment.

In yet another preferred embodiment, several divided doses may be administered daily. For example, three doses per day may be administered, preferably two doses per day. It is more preferred to administer a single dose per day.

In yet another preferred embodiment, an amount of the compounds of the present invention may be administered which results in a plasma concentration of 0.1 to 15 µg/ml (trough) and 5 to 18.5 µg/ml (peak), calculated as an average over a plurality of treated subjects.

The compounds of Formulae (Ib) or/and (IIb) may be administered in a convenient manner, such as by oral, intravenous (where water soluble), intramuscular, intrathecal or subcutaneous routes. Oral or/and i.v. administration is preferred.

The pharmaceutical composition of the present invention may be prepared for the treatment regimen as described above, in particular for the treatment with doses as described above, to effect plasma concentrations as described above, for administration periods or/and administration routes as specified in the embodiments of the present invention as described above.

In another preferred embodiment, the method of the present invention as described above for the treatment of a mammal including a human being in need thereof comprises administering a compound of the present invention in combination with administering a further active agent for the prevention, alleviation or/and treatment of trigeminal neuropathic pain. The compound of the present invention and the further active agent may be administered together, i.e. in a single dose form, or may be administered separately, i.e. in a separate dose form. Thus, the pharmaceutical composition of the present invention may comprise a compound of the present invention as defined above and may further comprise a further active agent for the prevention, alleviation or/and treatment of trigeminal neuropathic pain. The pharmaceutical composition may comprise a single dose form or may comprise a separate dose form comprising a first composition comprising a compound of the present invention as defined above and a second composition comprising the further active agent.

The compounds of the present invention may be used for the preparation of a pharmaceutical composition as described above.

The compounds of Formulae (Ib) or/and (IIb) may be orally administered, for example, with an inert diluent or with an assimilable edible carrier, or it may be enclosed in hard or soft shell gelatin capsules, or it may be compressed into tablets, or it may be incorporated directly into the fool of the diet. For oral therapeutic administration, the active compound of Formulae (Ib) or/and (IIb) may be incorporated with excipients and used in the form of ingestible tablets, buccal tablets, troches, capsules, elixirs, suspensions, syrups, wafers, and the like. Such compositions and preparations should contain at least 1% of active compound of Formulae (Ib) or/and (IIb). The percentage of the compositions and preparations may, of course, be varied and may conveniently be between about 5 to about 80% of the weight of the unit. The amount of active compound of Formulae (Ib) or/and (IIb) in such therapeutically useful compositions is such that a suitable dosage will be obtained. Preferred compositions or preparations according to the present invention contains between about 10 mg and 6 g active compound of Formulae (Ib) or/and (IIb).

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying the freeze-drying technique plus any additional desired ingredient from previously sterile-filtered solution thereof.

As used herein, "pharmaceutically acceptable carrier" includes any and all solvents, dispersion media, coatings, antibacterial and antifungal agent, isotonic and absorption delaying agents for pharmaceutical active substances as well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is a human.

The term "treat" refers to either relieving the pain associated with a disease or condition or alleviating the patient's disease or condition.

The compounds of the present invention are administered to a patient suffering from the aforementioned type of pain in an analgesic effective amount. These amounts are equivalent to the therapeutically effective amounts described hereinabove.

The following example shows the properties of SPM 927 in reducing trigeminal pain in a rats with ischemic infraorbital nerve injury.

The used substance was SPM 927 which is the synonym for Harkoseride. The standard chemical nomenclature is (R)-2-acetamide-N-benzyl-3-methoxypropionamide.

FIGURE LEGEND

FIG. 1 shows the effect (median±median absolute deviation, M.A.D.) of administration of vehicle (n=23 males, open circles) or SPM 927 at 7.5 mg/kg (open circles, 7 females), SPM 927 at 15 (open squares, 7 females, 8 males), 20 (filled circles, 7 females, 7 males) and 30 mg/kg (filled squares, 15 males) on vocalization threshold to stimulation with von Frey hairs in male (A) and female (B) rats after infraorbital (IoN) nerve injury. *=$p<0.05$ and **=$p<0.01$ compared to baseline at time 0 with Wilcoxon signed-ranks test.

EXAMPLE

The present study, shows the analgesic effects SPM 927 in a rat model of injury to the infraorbital nerve (IoN) which is regarded as a model of trigeminal neuropathic pain.

Materials and Methods

Male and female Sprague-Dawley rats (Möllegård, Denmark) weighing 200-250 g at the start of the experiments were used. All experimental procedures were approved by the local research ethics committee.

Photochemically-Induced Ischemic Infraorbital Nerve (IoN) Injury

Rats were anesthetized with chloral hydrate. The left IoN was exposed via a longitudinal incision at the maxillary region and all branches of the nerve were carefully lifted on a glass hook. A piece of aluminium foil was placed under the nerve and the nerve was irradiated for 6 min with the tunable argon ion laser. The rat was positioned so that the laser beam was perpendicular and transversal to the exposed nerve. Immediately before irradiation erythrosin B was injected i.v. and the injection was repeated after 5 min. After irradiation the wound was closed in layers.

Assessment of Mechanical Sensitivity after IoN Injury

Mechanical sensitivity was tested with a series of von Frey filaments. The rat was gently held by the experimenter and the von Frey filaments were applied in ascending order to the IoN territory on the hairy skin of the vibrissal pad. The stimulation with each filament consisted of four consecutive applications at 1/s on the injured and then on the contralateral side. The response threshold was taken as the force at which the rat either exhibited a withdrawal reaction or escape/attack in 75% of trials (Vos et al. 1994). The rats were habituated to the testing procedure for several days before nerve injury and baseline response was determined in two sessions. Testing was carried out 3, 7, 10 and 14 d after the injury to assess the development of mechanical hypersensitivity. The effect of SPM 927 (7.5, 15, and 30 mg/kg) was tested 14-16 days after injury when mechanical hypersensitivity was well established. Measurements were taken 30 min, 1 h, 2 h, and 3 h following drug injection.

Drugs and Statistics

SPM 927 was dissolved in physiological saline and injected intraperitoneally. The data are expressed as median±M.A.D. and analysed with Wilcoxon signed-ranks test.

Results

Effects of SPM 927 on Mechanical Hypersensitivity after IoN Injury

Figure 1B:
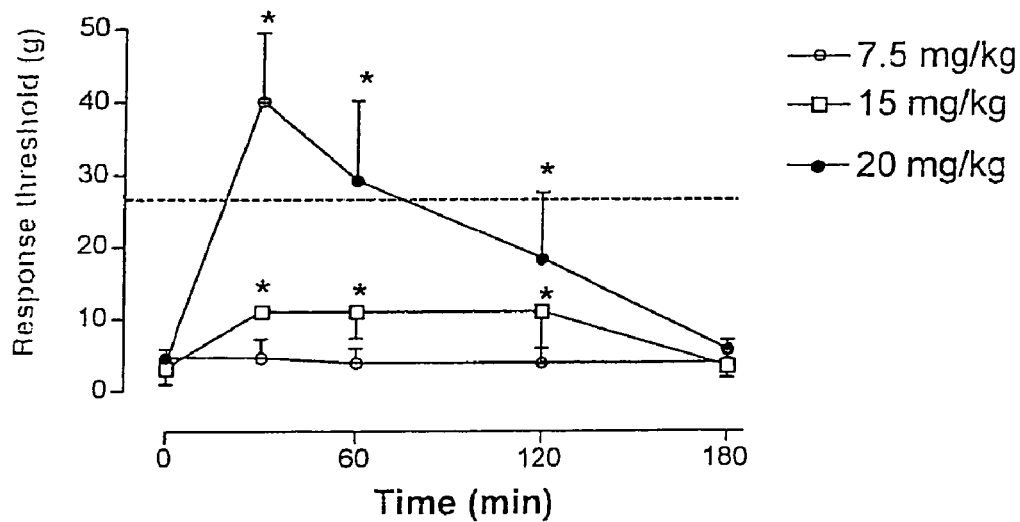

Partial injury to the IoN leads to the development of mechanical hypersensitivity in the innervation area of the nerve. Normal response threshold to mechanical stimulation was between 18-40 g whereas after injury, the response threshold decreased significantly for both male and female rats (median 5.8 g and 4.0 g respectively). The mechanical hypersensitivity developed rapidly after IoN nerve injury, reaching peak level within 3 days and was stable thereafter for at least 3-4 weeks with the irradiation parameter used in the present study. In male rats SPM 927 at 15 or 20 mg/kg did not alleviate mechanical hypersensitivity whereas at 30 mg/kg it significantly alleviated mechanical hypersensitivity for 3 h (FIG. 1A). In female rats, SPM 927 significantly and markedly alleviated mechanical hypersensitivity at doses of 15 or 20 mg/kg whereas it has no effect at 7.5 mg/kg (FIG. 1B). SPM 927 did not cause motor deficits.

CONCLUSION

Systemic SPM 927 produced a dose-dependent analgesic or/and anti-allodynic effect in a rat model of trigeminal neuropathic pain following single dose administration. Thus, SPM 927 and related compounds are useful for the treatment of pain during trigeminal neuralgia in mammals including humans. As this nerve injury can be regarded as a model for a mononeuropathy, SPM 927 and related compounds are also useful for the treatment of pain resulting from neuropathies of other nerves (mononeuropathies). Furthermore, it can be regarded as an extended model for atypical facial pain. Consequently, SPM 927 and related compounds are useful for the treatment of atypical facial pain.

REFERENCES

Vos, B. P., Strassmann, A. M. and Maciewicz R. J. Behavioral evidence of trigeminal neuropathic pain following chronic constriction injury to the rat's infraorbital nerve. *J. Neurosci.* 1994; 14:2708-2323.

The invention claimed is:

1. A method for alleviating and/or treating atypical facial pain in a subject in need of such alleviation and/or treatment, the method comprising administering to the subject a compound of Formula (IIb)

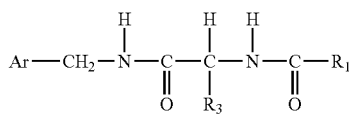

Formula (IIb)

wherein
Ar is phenyl which is unsubstituted or substituted with at least one halo group;
$R_3$ is $CH_2$-Q, wherein Q is lower a containing 1-3 carbon atoms; and
$R_1$ is lower alkyl containing 1-3 carbon atoms,
or a pharmaceutically acceptable salt thereof.

2. The method of claim 1 wherein, in the compound of Formula (IIb), Ar is unsubstituted phenyl.

3. The method of claim 1 wherein, in the compound of Formula (IIb), halo is fluoro.

4. The method of claim 1 wherein, in the compound of Formula (IIb), $R_3$ is $CH_2$-Q, wherein Q is alkoxy containing 1-3 carbon atoms, and Ar is unsubstituted phenyl.

5. The method of claim 1, wherein the compound of Formula (IIb) is (R)-2-acetamido-N-benzyl-3-methoxypropionamide.

6. The method of claim 5 wherein the compound is substantially enantiopure.

7. The method of claim 1, wherein the compound is administered at increasing daily doses until a predetermined daily dose is reached which is maintained during further treatment.

8. The method of claim 1, wherein the compound is administered in no more than three doses per day.

9. The method of claim 5, wherein the compound is administered in an amount resulting in a plasma concentration of the compound of 0.1 to 15 μg/ml (trough) and 5 to 18.5 μg/ml (peak).

10. The method of claim 1, wherein the compound is administered orally or intravenously.

11. The method of claim 1, wherein the subject is a mammal.

12. The method of claim 11 wherein the subject is a human.

13. The method of claim 1, wherein the compound of Formula (IIb) or a pharmaceutically acceptable salt thereof is administered in a dosage amount of about 50 mg/day to about 1 g/day.

14. The method of claim 13, wherein the compound of Formula (IIb) or a pharmaceutically acceptable salt thereof is administered in a dosage amount of about 200 mg/day to about 1 g/day.

15. The method of claim 14, wherein the compound of Formula (IIb) or a pharmaceutically acceptable salt thereof is administered in a dosage amount of about 200 mg/day to about 600 mg/day.

16. The method of claim 14, wherein the compound of Formula (IIb) is (R)-2-acetamido-N-benzyl-3-methoxypropionamide in an oral dosage amount of about 50 mg/day to about 600 mg/day.

17. The method of claim 16, wherein the dosage amount is about 200 mg/day to about 600 mg/day.

18. The method of claim 1, wherein the compound is selected from the group consisting of
(R)-2-acetamido-N-benzyl-3-methoxy-propionamide;
O-methyl-N-acetyl-D-serine-m-fluorobenzylamide; and
O-methyl-N-acetyl-D-serine-p-fluorobenzylamide.

* * * * *

UNITED STATES PATENT AND TRADEMARK OFFICE
CERTIFICATE OF CORRECTION

PATENT NO. : 8,338,641 B2  Page 1 of 1
APPLICATION NO. : 12/816753
DATED : December 25, 2012
INVENTOR(S) : Thomas Stöhr et al.

It is certified that error appears in the above-identified patent and that said Letters Patent is hereby corrected as shown below:

In the Specification

Column 1, line 48, replace "$NR_4OR_8$" with --$NR_4OR_5$--.

Column 4, line 48, replace "$R_7$ is $R_5$" with --$R_7$ is $R_6$--.

Column 9, line 49, replace "O-1,2" with --D-1,2--.

Column 15, line 8, replace "(7.5, 15, and 30 mg/kg)" with --(7.5, 15, 20 and 30 mg/kg)--.

In the Claims

Column 16, Claim 1, line 12, replace "Q is lower a containing" with --Q is lower alkoxy containing--.

Signed and Sealed this
Thirtieth Day of July, 2013

Teresa Stanek Rea
*Acting Director of the United States Patent and Trademark Office*